(12) United States Patent
Cox et al.

(10) Patent No.: US 10,952,689 B2
(45) Date of Patent: Mar. 23, 2021

(54) MULTI-AXIS LINEAR X-RAY IMAGING SYSTEM

(71) Applicant: PRINCIPLE IMAGING CORPORATION, West Yellowstone, MT (US)

(72) Inventors: John D. Cox, Gainesville, FL (US); Iain Hueton, Ogden, UT (US); Gary R. Cantu, West Yellowstone, MT (US)

(73) Assignee: PRINCIPLE IMAGING CORPORATION, West Yellowstone, MT (US)

( * ) Notice: Subject to any disclaimer, the term of this patent is extended or adjusted under 35 U.S.C. 154(b) by 599 days.

(21) Appl. No.: 15/618,818

(22) Filed: Jun. 9, 2017

(65) Prior Publication Data

US 2018/0055467 A1   Mar. 1, 2018

Related U.S. Application Data

(60) Provisional application No. 62/348,686, filed on Jun. 10, 2016, provisional application No. 62/478,347, filed on Mar. 29, 2017.

(51) Int. Cl.
*A61B 6/00* (2006.01)
*A61B 6/06* (2006.01)
(Continued)

(52) U.S. Cl.
CPC ............ *A61B 6/4458* (2013.01); *A61B 6/032* (2013.01); *A61B 6/035* (2013.01); *A61B 6/06* (2013.01); *A61B 6/08* (2013.01); *A61B 6/40* (2013.01); *A61B 6/4007* (2013.01); *A61B 6/4014* (2013.01); *A61B 6/4035* (2013.01); *A61B 6/4078* (2013.01); *A61B 6/42* (2013.01); *A61B 6/4208* (2013.01); *A61B 6/4216* (2013.01); *A61B 6/4266* (2013.01); *A61B 6/44* (2013.01); *A61B 6/4405* (2013.01); *A61B 6/4411* (2013.01); *A61B 6/4429* (2013.01); *A61B 6/4435* (2013.01); *A61B 6/4441* (2013.01); *A61B 6/4452* (2013.01); *A61B 6/4464* (2013.01); *A61B 6/4476* (2013.01);
(Continued)

(58) Field of Classification Search
CPC .......... A61B 6/032; A61B 6/035; A61B 6/44; A61B 6/4405; A61B 6/4429; A61B 6/4435; A61B 6/4452; A61B 6/4458; A61B 6/4464; A61B 6/4476; A61B 6/508; A61B 6/40; A61B 6/4007; A61B 6/4014; A61B 6/42; A61B 6/4208; A61B 6/4266; A61B 6/4411; A61B 6/4441; G01N 23/04; G01N 23/046; G01V 5/0016; G01V 5/005; G01V 5/0066
USPC ............ 378/57, 62, 189, 196–198, 9, 10, 19
See application file for complete search history.

(56) References Cited

U.S. PATENT DOCUMENTS 6,155,713 A * 12/2000 Watanabe ............ A61B 6/4441
                                                     378/197
6,200,024 B1 * 3/2001 Negrelli ............... A61B 6/4233
                                                     378/196

(Continued)

*Primary Examiner* — Allen C. Ho
(74) *Attorney, Agent, or Firm* — Rimon Law (57) ABSTRACT

Systems for large animal fluoroscopy having independently positionable X-ray emitter and X-ray detector arms on either side of the animal providing independent movement of the X-ray emitter and X-ray detector in multiple degrees of freedom.

21 Claims, 11 Drawing Sheets

(51) Int. Cl.
*A61B 6/08* (2006.01)
*G01N 23/046* (2018.01)
*G01V 5/00* (2006.01)
*A61B 6/03* (2006.01)
*G01N 23/04* (2018.01)

(52) U.S. Cl.
CPC ............ *A61B 6/4488* (2013.01); *A61B 6/508* (2013.01); *A61B 6/542* (2013.01); *A61B 6/587* (2013.01); *G01N 23/04* (2013.01); *G01N 23/046* (2013.01); *G01V 5/005* (2013.01); *G01V 5/0016* (2013.01); *G01V 5/0066* (2013.01); *A61B 6/4233* (2013.01)

(56) References Cited

U.S. PATENT DOCUMENTS

| | | | | |
|---|---|---|---|---|
| 6,236,709 | B1* | 5/2001 | Perry | G01N 23/046 378/25 |
| 6,435,715 | B1* | 8/2002 | Betz | A61B 6/4458 378/197 |
| 6,453,003 | B1* | 9/2002 | Springer | G01N 23/06 378/57 |
| 6,496,558 | B2* | 12/2002 | Graumann | A61B 6/0478 378/197 |
| 6,582,121 | B2* | 6/2003 | Crain | A61B 6/107 378/189 |
| 6,592,259 | B2* | 7/2003 | Crain | A61B 6/107 378/196 |
| 6,644,852 | B2* | 11/2003 | Crain | A61B 6/107 378/193 |
| 6,733,176 | B2* | 5/2004 | Schmitt | A61B 6/4464 378/196 |
| 6,763,083 | B2* | 7/2004 | Fernandez | G01V 5/0058 378/196 |
| 6,872,000 | B2* | 3/2005 | Atzinger | A61B 6/4233 378/197 |
| 6,934,352 | B2* | 8/2005 | Freytag | A61B 6/032 378/4 |
| 7,182,511 | B2* | 2/2007 | Boomgaarden | A61B 6/4464 378/197 |
| 7,401,977 | B2* | 7/2008 | Graumann | A61B 6/4441 378/197 |
| 7,441,953 | B2* | 10/2008 | Banks | A61B 5/1038 378/197 |
| 7,505,562 | B2* | 3/2009 | Dinca | G01N 23/201 378/57 |
| 7,526,064 | B2* | 4/2009 | Akery | G01V 5/0016 378/57 |
| 7,606,348 | B2* | 10/2009 | Foland | G01N 23/046 378/4 |
| 7,643,612 | B2* | 1/2010 | Benndorf | A61B 6/4233 378/207 |
| 7,806,589 | B2* | 10/2010 | Tashman | A61B 5/1038 378/193 |
| 7,809,109 | B2* | 10/2010 | Mastronardi | G01N 23/201 378/90 |
| 7,826,589 | B2* | 11/2010 | Kotowski | G01V 5/0025 378/57 |
| 7,831,012 | B2* | 11/2010 | Foland | G01N 23/04 378/57 |
| 7,949,094 | B2* | 5/2011 | Ahn | A61B 6/447 378/197 |
| 7,988,357 | B2* | 8/2011 | Hornung | A61B 6/4233 378/197 |
| 8,201,999 | B2* | 6/2012 | Uchida | A61B 6/547 378/197 |
| 8,290,119 | B2* | 10/2012 | Tancredi | A61B 6/14 378/197 |
| 8,360,639 | B2* | 1/2013 | Kato | A61B 6/4233 378/197 |
| 8,449,183 | B2* | 5/2013 | Seimiya | A61B 6/4464 378/196 |
| 8,529,128 | B2* | 9/2013 | Horiuchi | A61B 6/4482 378/196 |
| 8,553,842 | B2* | 10/2013 | Moon | A61B 6/4464 378/115 |
| 8,651,740 | B2* | 2/2014 | Yang | A61B 6/4405 378/197 |
| 8,944,680 | B2* | 2/2015 | Graumann | A61B 6/4452 250/491.1 |
| 8,950,937 | B2* | 2/2015 | Okuno | A61B 6/06 378/114 |
| 9,028,144 | B2* | 5/2015 | Choi | A61B 6/032 378/205 |
| 9,044,604 | B2* | 6/2015 | Dirauf | A61B 6/032 |
| 9,050,023 | B2* | 6/2015 | Okuno | A61B 6/08 |
| 9,121,809 | B2* | 9/2015 | Cox | G01N 23/04 |
| 9,125,611 | B2* | 9/2015 | Eaves | A61B 6/4405 |
| 9,144,406 | B2* | 9/2015 | Dennerlein | A61B 6/025 |
| 9,277,900 | B2* | 3/2016 | Kim | A61B 6/4482 |
| 9,453,936 | B2* | 9/2016 | Smith | G01V 5/0025 |
| 9,521,983 | B2* | 12/2016 | Jang | A61B 6/4429 |
| 9,649,080 | B2* | 5/2017 | Kwak | A61B 6/4429 |
| 9,655,575 | B2* | 5/2017 | Park | A61B 6/4233 |
| 9,757,080 | B2* | 9/2017 | Lee | A61B 6/462 |
| 10,076,290 | B2* | 9/2018 | Lee | A61B 6/547 |
| 10,098,609 | B2* | 10/2018 | Kim | A61B 6/06 |
| 10,136,866 | B2* | 11/2018 | Onobori | A61B 6/4458 |
| 10,136,870 | B2* | 11/2018 | Ray | A61B 6/508 |
| 10,136,871 | B2* | 11/2018 | Yorkston | A61B 6/508 |
| 10,172,579 | B2* | 1/2019 | Yang | A61B 6/4429 |
| 10,182,778 | B2* | 1/2019 | Jang | F16M 11/046 |
| 10,258,307 | B2* | 4/2019 | Park | A61B 6/547 |
| 10,338,238 | B2* | 7/2019 | Kim | A61B 6/44 |
| 10,398,401 | B2* | 9/2019 | Okuno | A61B 6/547 |
| 10,561,384 | B2* | 2/2020 | Tanaka | A61B 6/4452 |
| 10,702,229 | B2* | 7/2020 | Lee | A61B 6/542 |
| 10,743,827 | B2* | 8/2020 | Kumar | A61B 6/467 |

* cited by examiner

MULTI-AXIS LINEAR X-RAY IMAGING SYSTEM

RELATED APPLICATION

The present application claims priority to U.S. Provisional Patent Application Ser. No. 62/348,686, entitled MODULAR LARGE-BORE COMPUTED TOMOGRAPHY IMAGING SYSTEM, filed Jun. 10, 2016, and Ser. No. 62/478,347, entitled A MULTI-AXIS LINEAR X-RAY IMAGING SYSTEM, filed Mar. 29, 2017, the entire disclosures of which are incorporated herein by reference in their entirety for all purposes.

TECHNICAL FIELD

The present system relates to scanning radiographic imaging in general and to large animal veterinary radiographic imaging systems in particular.

BACKGROUND OF THE INVENTION

Obtaining radiographic images in the abdominal and thoracic cavities of large animals such as horses presents many challenges. First, as prey animals, horses are typically rather nervous and often do not willfully submit to placement within (e.g.: r between the arms of) a large frame imaging system. Moreover, should the horse become agitated in this situation, there is a real danger of the horse panicking and attempting to flee. This presents a huge safety risk as a panicked horse represents a danger not only to themselves, but also to the veterinarian attempting to image the horse. Additionally, a panicked horse can also very easily damage sensitive expensive equipment. To date, there has been no easy way to obtain radiographic images within the abdominal cavity of horses. In addition, conventional Computed Tomography (CT) systems are huge pieces of equipment that must fully encircle at least the body part of the horse being scanned. Even if the horse is not panicked, it is still somewhat difficult to position a large animal within the framework of an even larger machine.

As a result, the common "solution" to obtaining images of the horse is to have the horse anesthetized, immobilized and transported to an overhead tube crane for radiographic imaging (for images of the hip). As can be appreciated, this approach is costly, time consuming and risky. It would instead be desirable to perform the scan with the horse in a sedated, but standing, load-bearing position. It would also be desirable to have a system that can quickly be removed from the proximity of the animal should the animal become agitated.

Secondly, it is also difficult to image a large animal such as a horse due to the effect of X-ray scattering within the horse. Such X-ray scattering results in poor-quality images. X-ray scatter in horses is especially problematic when large areas of the thorax, abdominal or orthopedic examination of the spine or hips is required. One purported solution to this problem is to take the image scans through narrower sections of the body mass of the horse. Unfortunately, this is not entirely easy to accomplish as it requires complex positioning of the X-ray emitter and X-ray detector with respect to the horse's body. Using such an approach thus requires a highly positionable X-ray scanning system. Unfortunately, current designs are somewhat limited in terms of their actual positionability. What is instead desired is a system that provides more positioning options in terms of the placement both of the X-ray emitter and of the X-ray detector.

Typical conventional CT imaging systems also suffer from other disadvantages. For example, conventional C-arm systems have an emitter at one end of the C-frame and a detector at the other end of the C-frame. As such, the C-arm section must be a complete half circle such that the emitter and detector are positioned 180 degrees apart. What is desired is a simple, easy to use imaging system that provides a very high degree of positionability of the X-ray emitter and X-ray detector (such that images can be taken from many different angles through the animal to obtain the best image quality). It is also desired that the imaging system itself takes up little space around the (preferably standing) animal.

SUMMARY OF THE INVENTION

The present invention provides various scanning radiographic imaging systems that are well suited for imaging large animals such as horses.

The present system comprises an X-ray imaging system comprising a pair of independent spaced-apart arms dimensioned such that the animal can be positioned therebetween. In a first embodiment, these arms comprise an X-ray emitter arm and an X-ray detector arm. In a second embodiment, each of these arms has both an X-ray emitter and a linear (i.e.: flat or curved) X-ray detector thereon.

In a first preferred aspect, the imaging system comprises: (a) a multi-axis of motion X-ray emitter arm assembly, including: (i) an X-ray emitter, (ii) a yaw-axis of motion positioning system for pointing the X-ray emitter in different directions in a horizontal plane, (iii) a pitch-axis of motion positioning system for pointing the X-ray emitter up and down at different angles to a horizontal plane, (iv) a Z-axis assembly for moving the X-ray emitter up and down in a vertical direction; and (v) an X-axis assembly for moving the X-ray emitter back and forth in a horizontal direction; and (b) a multi-axis of motion X-ray detector arm assembly, including: (i) an X-ray detector, (ii) a yaw-axis of motion positioning system for pointing the X-ray detector in different directions in a horizontal plane, (iii) a pitch-axis of motion positioning system for pointing the linear X-ray detector up and down at different angles to a horizontal plane, (iv) a Z-axis assembly for moving the linear X-ray detector up and down in a vertical direction; and (v) an X-axis assembly for moving the linear X-ray detector back and forth in a horizontal direction.

Preferably, each of the X-ray emitter and the linear X-ray detector are mounted onto their own pitch-axis-of-motion-positioning systems which are in turn mounted onto the yaw-axis of motion positioning systems which are in turn mounted onto Z-axis of motion assemblies, which are in turn mounted onto X-axis of motion assemblies. Alternatively, one or both yaw-axes-of-motion-positioning systems can be mounted onto the pitch-axis-of-motion-positioning systems, all keeping within the scope of the present invention.

In accordance with the present system, the X-ray emitter and the X-ray detector can each be moved (up-down and left-right) to different positions within opposing vertical planes, and can be moved to be tilted to directly face one another. In various optional aspects, the X-axis assemblies for moving the X-ray emitter and the X-ray detector are mounted onto the ceiling of a room, or onto a frame supported by posts. As a result of this flexibility of positioning, an X-ray beam passing therebetween can be pointed in different directions in three mutually perpendicular axes in space. Preferably, in optional aspects, each of the arms further comprise roll-axis-of-motion-positioning systems for rotating the X-ray emitter and X-ray detector.

In preferred aspects, a collimator is included for producing a fan-shaped planar X-ray beam. Using the present positioning system, the plane of the fan-shaped planar X-ray beam is moveable in yaw, pitch and roll directions. As such, the X-ray emitter and linear X-ray detector can be positioned such that the plane of the fan-shaped planar X-ray beam is incident along the length of the linear X-ray detector. Preferably, the linear X-ray detector is a linear photodiode array or time-delayed-integration (TDI) photodiode array covered by scintillating material. In an alternative embodiment, the collimator can be configured to also produce a rectangular beam for use with a flat-panel detector to produce a traditional projection radiography image.

In further optional aspects, one or both assembly arms also comprise a Y-axis-of-motion assembly for increasing or decreasing the Y-axis separation distance between the assembly arms.

Advantages of this system include its ease of positioning around the horse, thereby allowing radiographic images to be taken of the horse when the horse is in a standing, sedated position. In addition, since the arms can be suspended from the ceiling, the amount of "hardware" around the animal is minimized. As such, the horse is less likely to feel trapped within an enclosure and less likely to panic.

In a second embodiment, the present system comprises a pair of arms with each arm having its own X-ray emitter and its own linear X-ray detector. In this embodiment, the arms also face one another with the horse being positioned therebetween.

As such, this second embodiment may comprise: (a) a first multi-axis of motion X-ray emitter and detector arm assembly, including: (i) an X-ray emitter, (ii) a curved or flat linear X-ray detector, and (iii) a positioning system for: (A) pointing the X-ray emitter and the linear X-ray detector up and down at different angles to a horizontal plane, and (B) moving the X-ray emitter and the X-ray detector up and down in a vertical direction; and (b) a second multi-axis of motion X-ray emitter and detector arm assembly, including: (i) an X-ray emitter, (ii) an X-ray detector, and (iii) a positioning system for: (A) pointing the X-ray emitter and the X-ray detector up and down at different angles to a horizontal plane, and (B) moving the X-ray emitter and the X-ray detector up and down in a vertical direction; wherein the first and second arms are positioned facing one another such that: the X-ray emitter on the first arm projects a fan-shaped X-ray beam onto the X-ray detector on the second arm, and the X-ray emitter on the second arm projects a fan-shaped X-ray beam on to the X-ray detector on the first arm. In an alternative embodiment, the linear curved X-ray detector is flat with no curvature. In still further alternative embodiments, one arm may have an X-ray emitter and the other arm have an X-ray detector, or both arms may each have their own X-ray emitter and X-ray detector.

Preferably, the positioning systems are robotic arms that are also configured for: (C) rotating the X-ray emitter and the linear X-ray detector around a vertical axis for pointing the X-ray emitter and the linear X-ray detector in different directions in a horizontal plane. A robotic base can be provided for (D) moving the X-ray emitter and the linear X-ray detector back and forth in a horizontal direction. Specifically, the positioning system for moving the X-ray emitter and the linear X-ray detector back and forth in a horizontal direction can comprise wheels on the robotic base, or the robotic base may be moveable horizontally on rails. The motion of the robotic base and positioning arms can also be controlled by a machine vision system that visualizes the volume of space occupied by the standing horse and robotic positioning system.

In preferred aspects, the X-ray emitter is positioned at a central location on the linear X-ray detector. Preferably, the curved linear detector arrays are positioned a distance apart such that an arc with a radius of curvature equal to the diameter of a circle passes through the detector arrays. As such, the length of each curved detector may preferably be ¼ of the circle of rotation of a comparable sized C-arm. As such, the present system provides a cylindrical detection surface with a radius of curvature similar to a CT scanner.

Advantages of this system include 360 degree CT image acquisition in a system having a small footprint that may even be portable (making the system very well suited for traveling veterinarians). As such, the present system reduces the size of the imaging system without compromising the ability to acquire full 360 degree CT images.

Moreover, in pre-existing systems, each base or side of the system has either an X-ray source or an X-ray detector (but not both). Accordingly, such systems must rotate or translate over large distances to capture high-fidelity images. In contrast, one particular illustrated embodiment of the present system has a pair of identical bases that each have an X-ray emitter and an X-ray detector connected thereto by a moveable robotic arm. (In other embodiments, one arm has an X-ray emitter and the other arm has an X-ray detector). In preferred methods of operation in the illustrated embodiment, the two detector arrays rotate through a pre-programmed arc and the wheels move along parallel tracks to acquire successive CT image slices of anatomic regions. As such, data can be acquired faster than in with conventional CT scanning system. In addition, existing Cone-beam CT systems use large-area detectors (flat panels or image intensifiers) for radiographic, fluoroscopic or tomographic images. Unfortunately, large area detectors suffer from poor image quality due to X-ray scatter (especially with large animals).

In optional embodiments, the present X-ray detector may contain more than one row of sensing elements or pixels to create multi-slice image acquisition with a single rotation of the robotic arms. A slit collimator can be positioned near the output of the X-ray tube, and a post-scatter collimator can be mounted on or near the detector array (to improve image quality).

Also included in various embodiments of the present system is a user interface for the operator to acquire, view and store images. A machine vision system with cameras and sensors can also be included to assist with positioning of the arms.

DETAILED DESCRIPTION OF THE DRAWINGS

Figure 14:
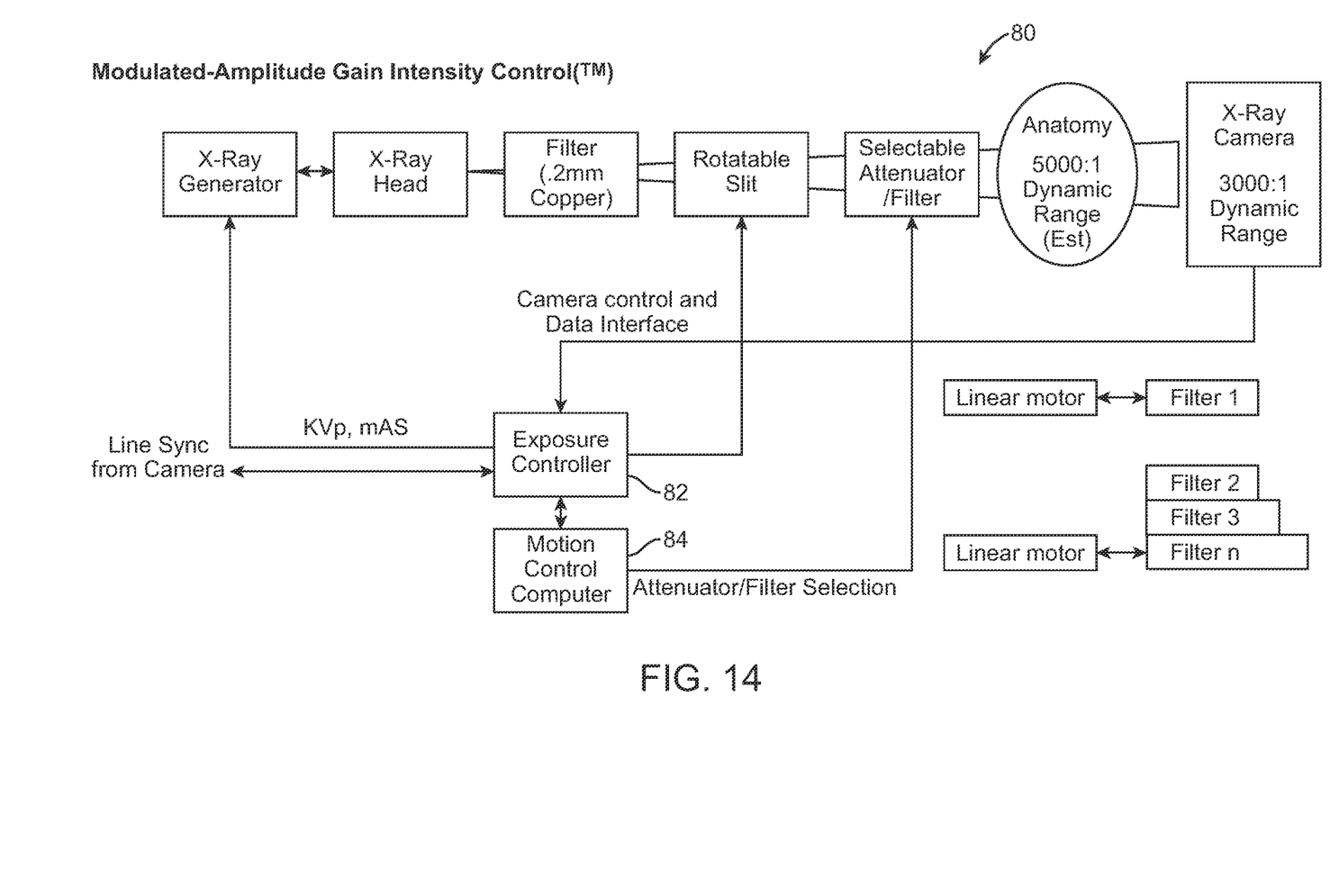
FIG. 14 is a schematic of an optional Modulated Amplitude Gain Intensity Control system for use with the present system.
Figure 15:
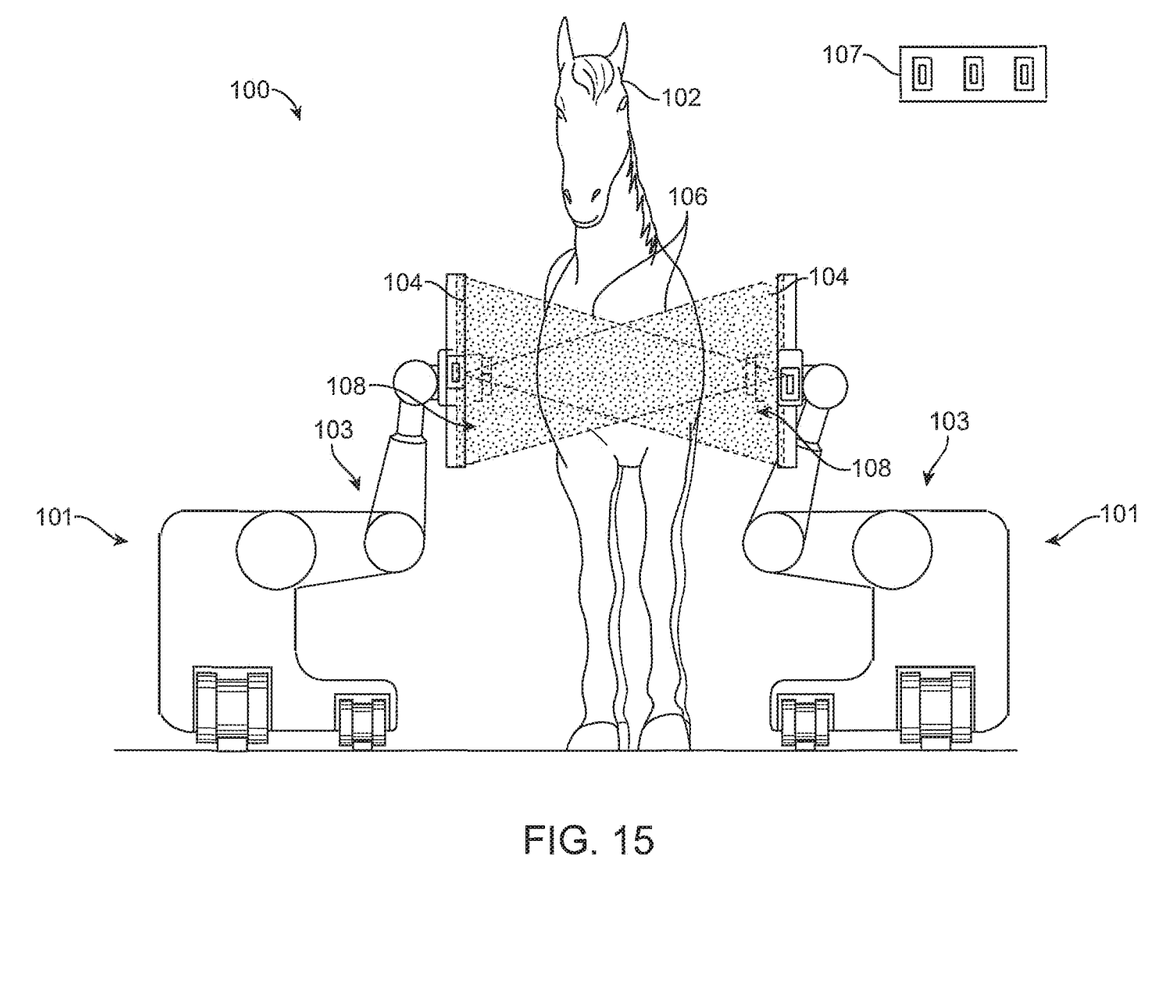
FIG. 15 is a front perspective view of a second embodiment of the present system.

FIGS. 1 to 14 present a first embodiment of the present system and FIG. 15 presents a second embodiment of the present system.

Figure 1:
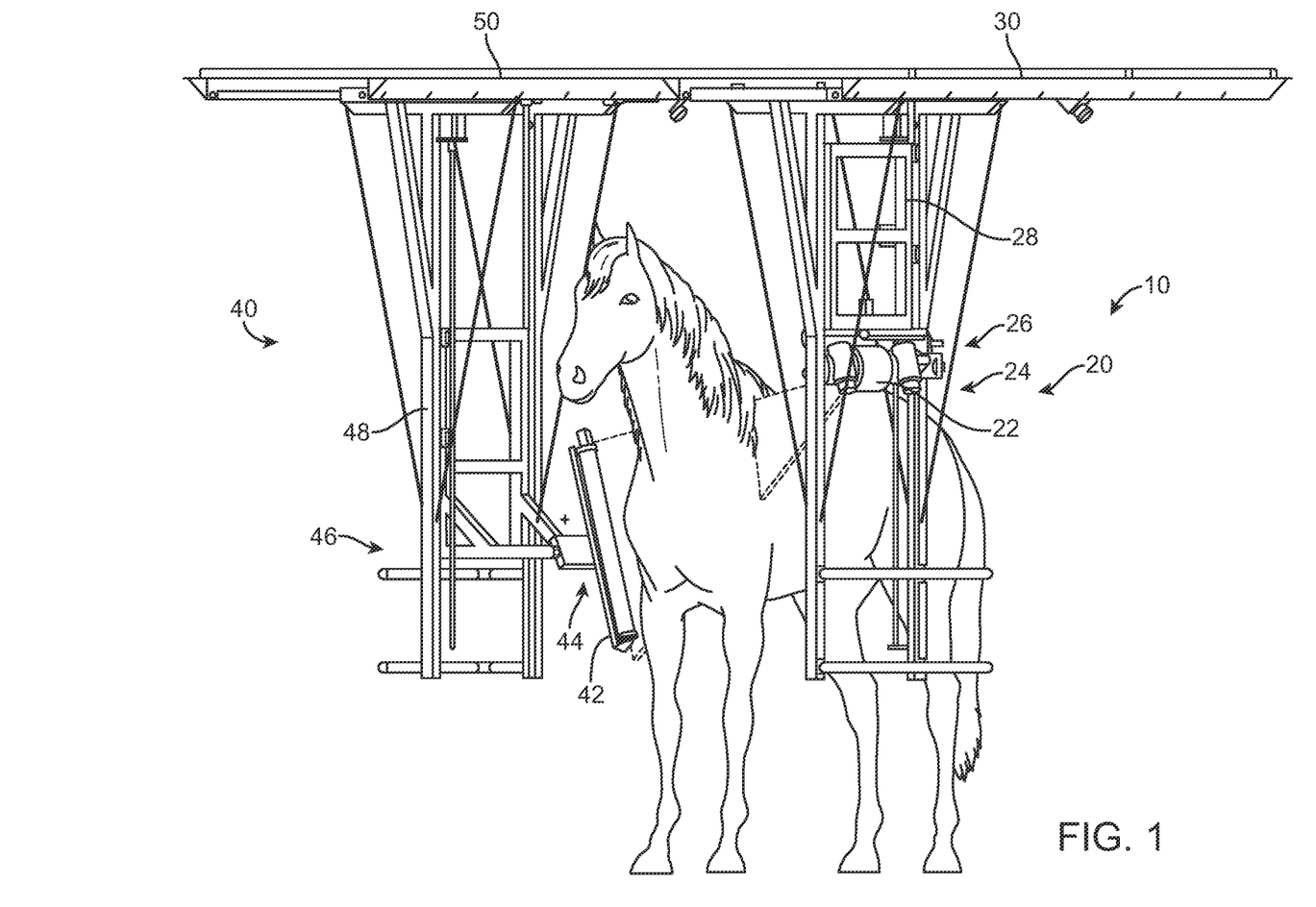
FIG. 1 is a perspective view of a first embodiment of the present imaging system.
Figure 2:
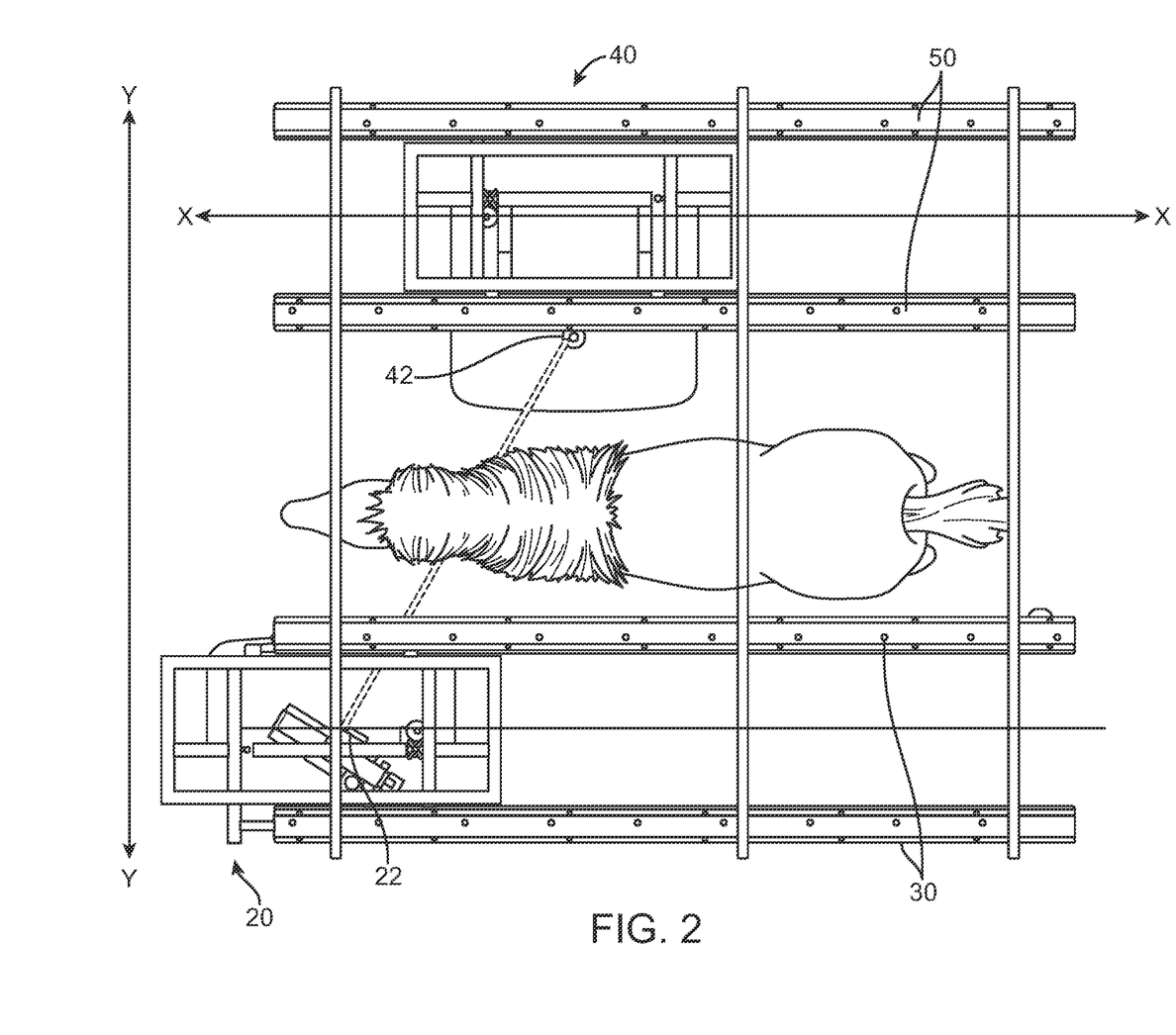
FIG. 2 is a top plan view corresponding to FIG. 1.

As seen in FIGS. 1 and 2, the present system provides an X-ray imaging system 10, comprising a multi-axis of motion X-ray emitter arm assembly 20 and a multi-axis-of-motion X-ray detector arm assembly 40. In optional embodiments, the present X-ray imaging system 10 provides 10 or 11 degrees of freedom to position and maneuver an X-ray emitter 22 and an X-ray detector 42.

Multi-axis-of-motion X-ray emitter arm assembly 20 may include: an X-ray emitter 22, a yaw-axis of motion positioning system 24 for pointing the X-ray emitter 22 in different directions in a horizontal plane, a pitch-axis of motion positioning system 26 for pointing the X-ray emitter 22 up and down at different angles to a horizontal plane, a Z-axis assembly 28 for moving the X-ray emitter 22 up and down in a vertical direction; and an X-axis assembly 30 for moving the X-ray emitter 22 back and forth in a horizontal direction.

Similarly, multi-axis of motion X-ray detector arm assembly 40, includes: an X-ray detector 42, a yaw-axis of motion positioning system 44 for pointing the X-ray detector 42 in different directions in a horizontal plane, a pitch-axis of motion positioning system 46 for pointing the X-ray detector 42 up and down at different angles to a horizontal plane, a Z-axis assembly 48 for moving the X-ray detector 42 up and down in a vertical direction; and an X-axis assembly 50 for moving the X-ray detector 42 back and forth in a horizontal direction.

Together, FIGS. 1 and 2 show an oblique lateral image being scanned through the thoracic region of the horse. The X-ray emitter 22 is elevated as compared to the X-ray detector 42 to acquire an image of the right shoulder of the horse. In this way, the left shoulder is out of view and not seen on this image.

X-ray emitter 22 and X-ray detector 42 are independently positionable. As a result, X-ray emitter 22 and X-ray detector 42 can be moved to different positions in opposing vertical planes (i.e.: X-ray emitter 22 and X-ray detector 42 can be moved in the X- and Z-directions). In addition, X-ray emitter 22 and X-ray detector 42 can be tilted to directly face one another. As such, an X-ray beam passing therebetween can be pointed in different directions in three mutually perpendicular axes in space.

As can be seen, X-axis assemblies 30 and 50 may optionally be mounted onto the ceiling of a room, or alternatively on a platform standing about 8 feet high with 4 posts fixed to the floor.

Figure 3A:
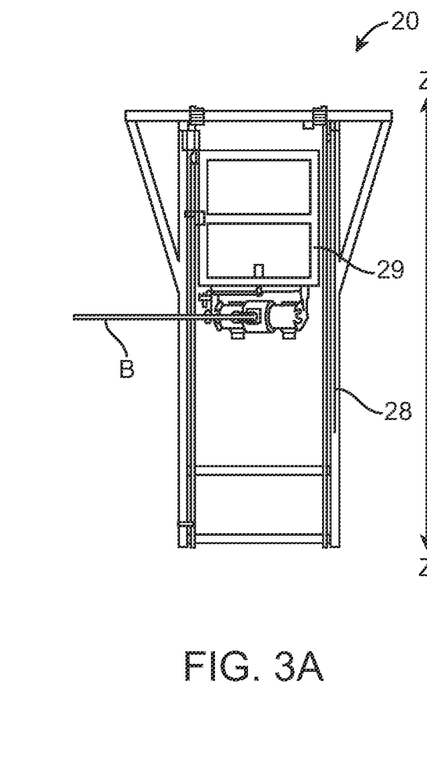
FIG. 3A is a side elevation view of the X-ray emitter in a raised position.
Figure 3B:
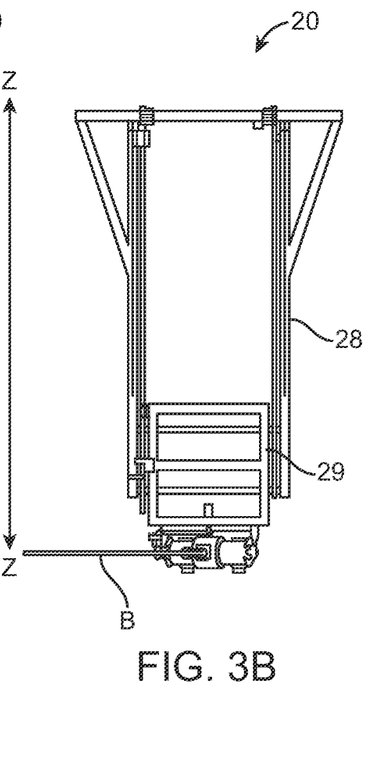
FIG. 3B is a side elevation view of the X-ray emitter in a lowered position.

FIGS. 3A and 3B show further details of Z-axis assembly 28 with frame 29 see in the fully raised position in FIG. 3A and in its fully lowered position in FIG. 3B. By moving frame 29 up and down within Z-axis assembly 28, the height of X-ray emitter 22 can be adjusted.

Figure 4A:
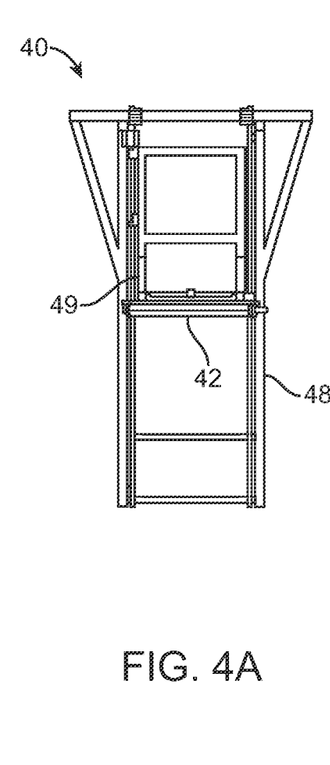
FIG. 4A is a side elevation view of the X-ray detector in a raised position.
Figure 4B:
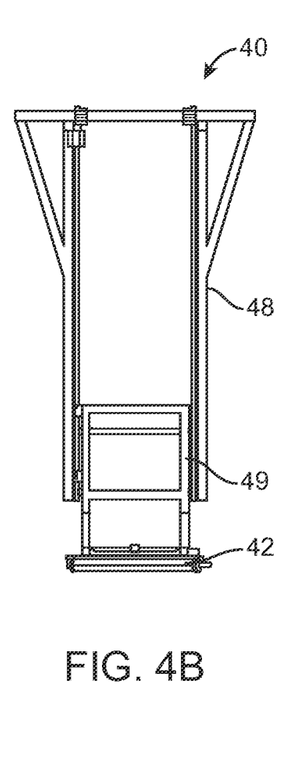
FIG. 4B is a side elevation view of the X-ray detector in a lowered position.

Similarly, FIGS. 4A and 4B show further details of Z-axis assembly 48 with frame 49 see in the fully raised position in FIG. 4A and in its fully lowered position in FIG. 4B. By moving frame 49 up and down within Z-axis assembly 48, the height of X-ray detector 42 can be adjusted.

As can be appreciated, frames 29 and 49 are independently moveable such that the beam passing therebetween does not have to be in a horizontal plane.

Figure 5:
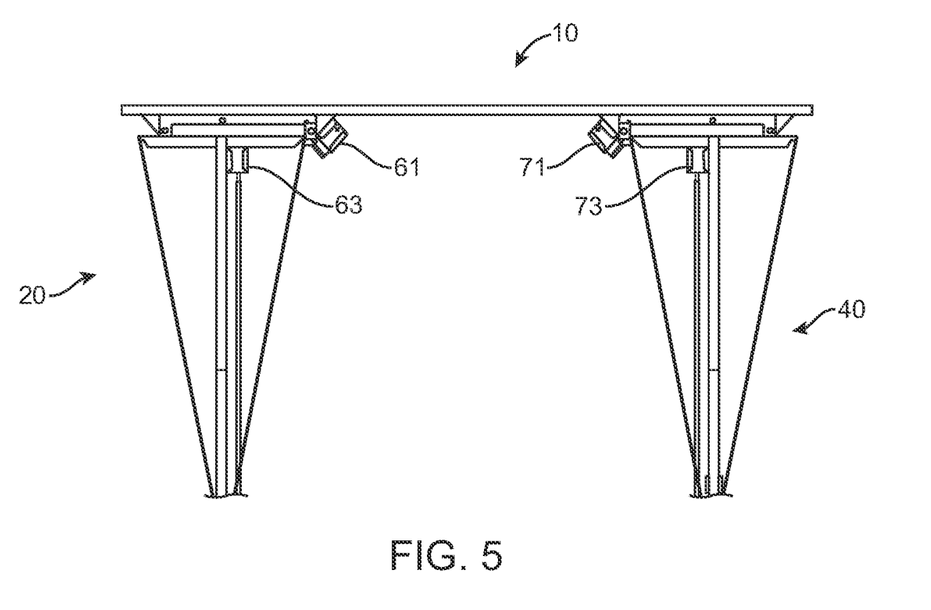
FIG. 5 is a front elevation view of the top portion of the first embodiment of the present imaging system.

FIG. 5 shows a view of the top portion of arms 20 and 40, showing: motor 61 for moving multi-axis-of-motion X-ray detector assembly arm 20 in the horizontal X-direction; motor 63 for moving frame 29 in the vertical Z-direction; motor 71 for moving multi-axis-of-motion X-ray detector assembly arm 40 in the horizontal X-direction; and motor 73 for moving frame 49 in the vertical Z-direction. Commercially available motion controllers manufactured by Quicksilver or Galil can be used for all motors with the position and motion accuracy required to obtain diagnostic quality images.

Figure 6:
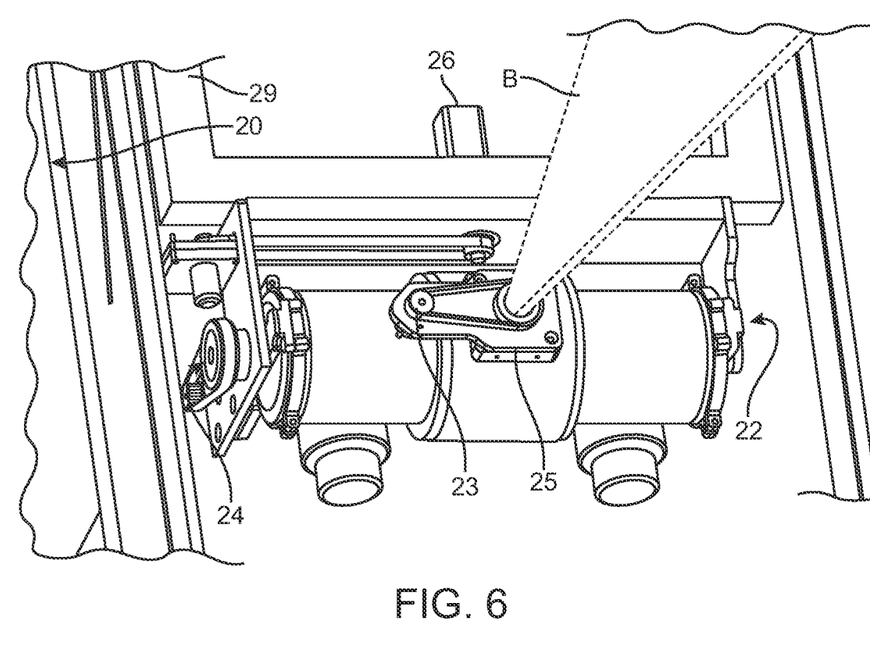
FIG. 6 is a perspective view showing the X-ray emitter and attached components of the first embodiment of the present imaging system.

FIG. 6 is a perspective view showing the X-ray emitter 22 and attached components of the first embodiment of the present X-ray imaging system 10. As can be seen, X-ray emitter 22 is mounted onto pitch-axis of motion positioning system 26 which is in turn mounted onto the yaw-axis of motion positioning system 24, which is in turn mounted onto the Z-axis assembly 28.

Figure 7A:
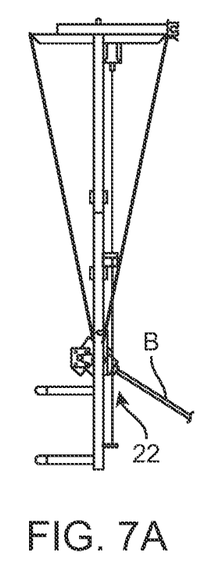
FIG. 7A is a side elevation view of the emitter arm, showing the X-ray beam pointed downwardly.
Figure 7B:
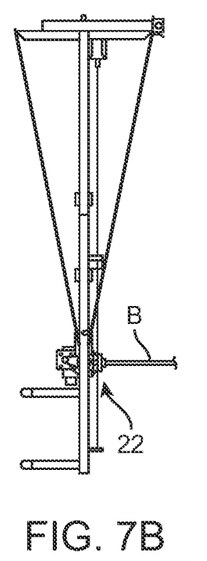
FIG. 7B is a side elevation view of the emitter arm, showing the X-ray beam pointed horizontally.
Figures 7C, 7D:
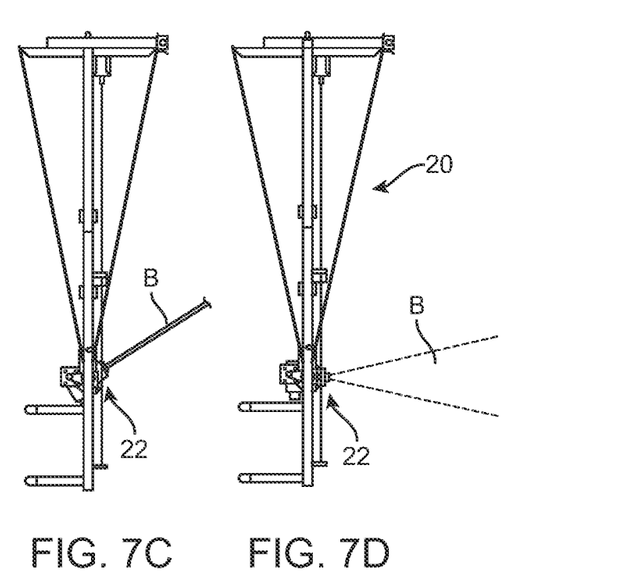
FIG. 7C is a side elevation view of the emitter arm, showing the X-ray beam pointed upwardly.
FIG. 7D is a side elevation view of the emitter arm, showing the X-ray beam rotated about a "roll-axis", showing the fan-shape of the beam.

FIGS. 7A to 7D show the positioning of the X-ray emitter 22 when pitch-axis of motion positioning system 26 is used to point the X-ray beam B in various directions. First, FIG. 7A shows the X-ray beam B pointed downwardly. Next, FIG. 7B shows the X-ray beam B pointed horizontally. Next, FIG. 7C shows the X-ray beam B pointed upwardly. Lastly, FIG. 7D shows the X-ray beam B rotated in a "roll" direction by roll-axis of motion positioning system 23. FIG. 7D thus shows the fan-shape of beam B (see also FIG. 6).

Figure 8A:
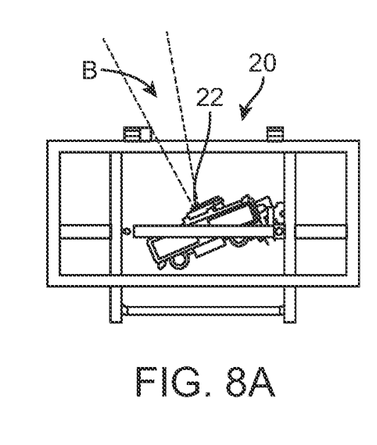
FIG. 8A is a top plan view of the emitter arm showing the X-ray beam rotated about a vertical "yaw-axis" to point in a first direction.
Figure 8B:
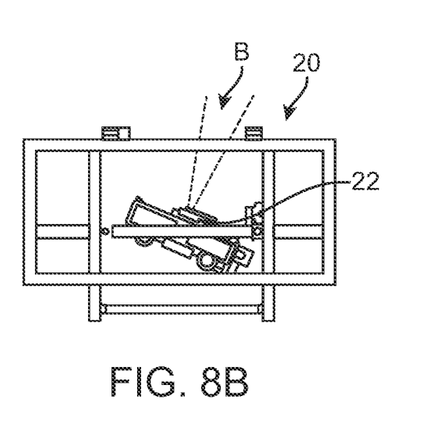
FIG. 8B is a top plan view of the emitter arm showing the X-ray beam rotated about a vertical "yaw-axis" to point in a second direction.

FIG. 8A is a top plan view of the multi-axis of motion X-ray emitter arm assembly 20 showing the X-ray beam B rotated about a vertical "yaw-axis" to point in a first direction, or in a second direction in FIG. 8B (see also yaw-axis of motion positioning system 24 in FIG. 6).

Figure 9:
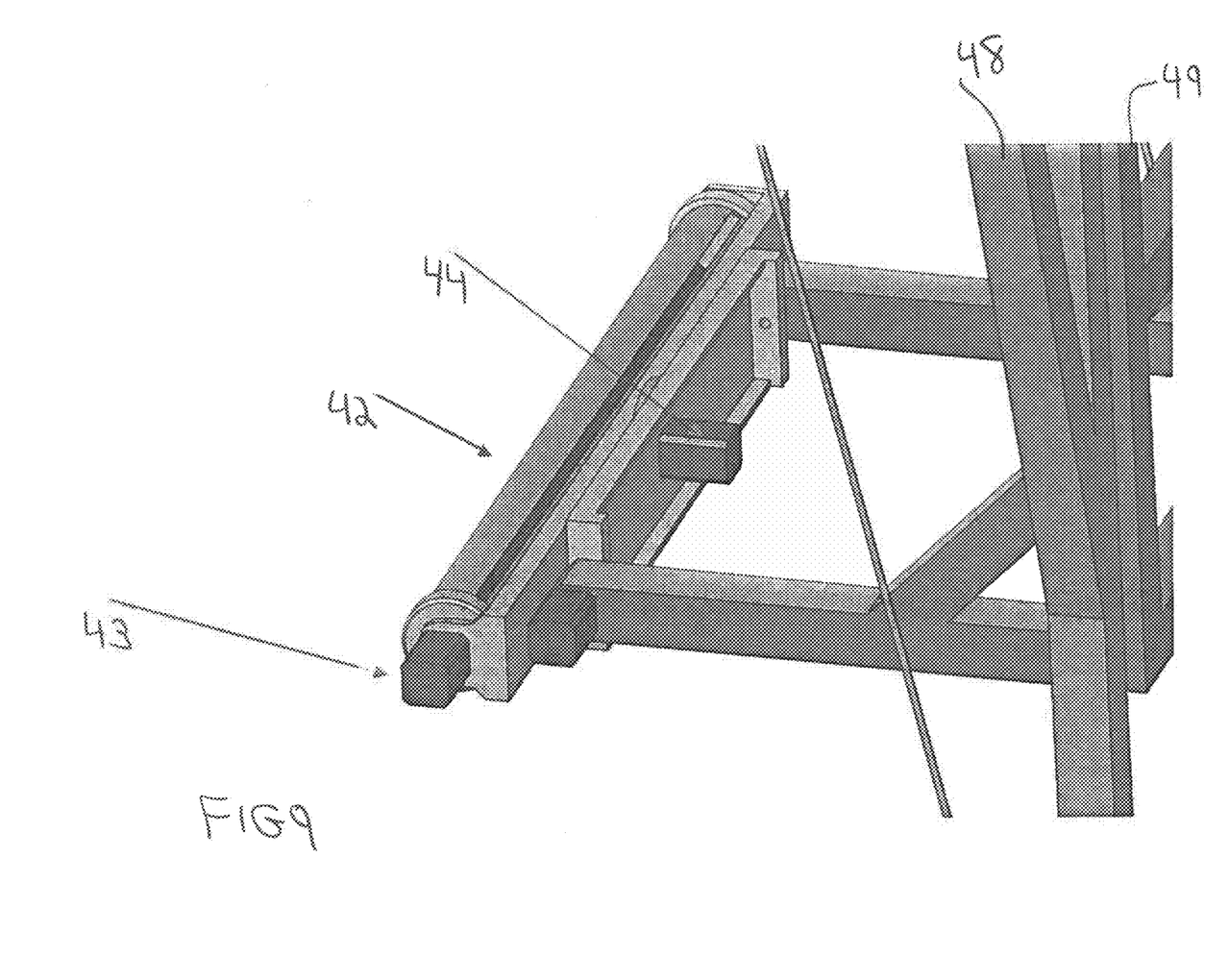
FIG. 9 is a perspective view showing the X-ray detector and attached components of the first embodiment of the present imaging system.

FIG. 9 is a perspective view showing the X-ray detector 42 and attached components of the first embodiment of the present X-ray imaging system 10. X-ray detector 42 is mounted onto the roll-axis of motion positioning system 43, which is in turn mounted onto the yaw-axis of motion positioning system 44, and wherein the yaw-axis of motion positioning system 44 is mounted onto the Z-axis assembly 48, with the Z-axis assembly 48 mounted onto the X-axis assembly 50 (FIGS. 1 and 2).

Figure 10A:
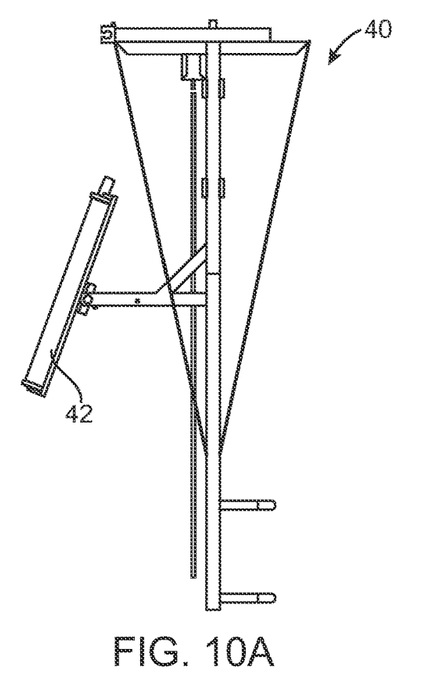
FIG. 10A is a side elevation view of the detector arm, showing the X-ray detector rotated about a pitch-axis to point upwardly.
Figure 10B:
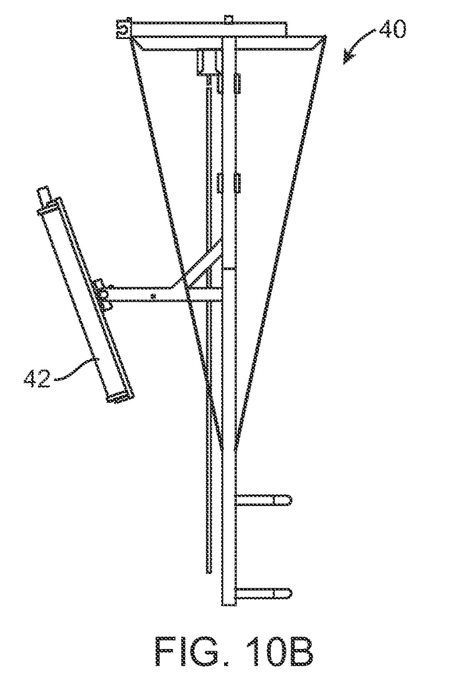
FIG. 10B is a side elevation view of the detector arm, showing the X-ray detector rotated about a pitch-axis to point downwardly.

FIGS. 10A and 10B are side elevation views of the detector arm 40, showing the X-ray detector rolled about its pitch-axis by positioning system 46 to be pointed to a first position (FIG. 10A) or to a second position (FIG. 10B).

Figures 11A, 11B, 12:
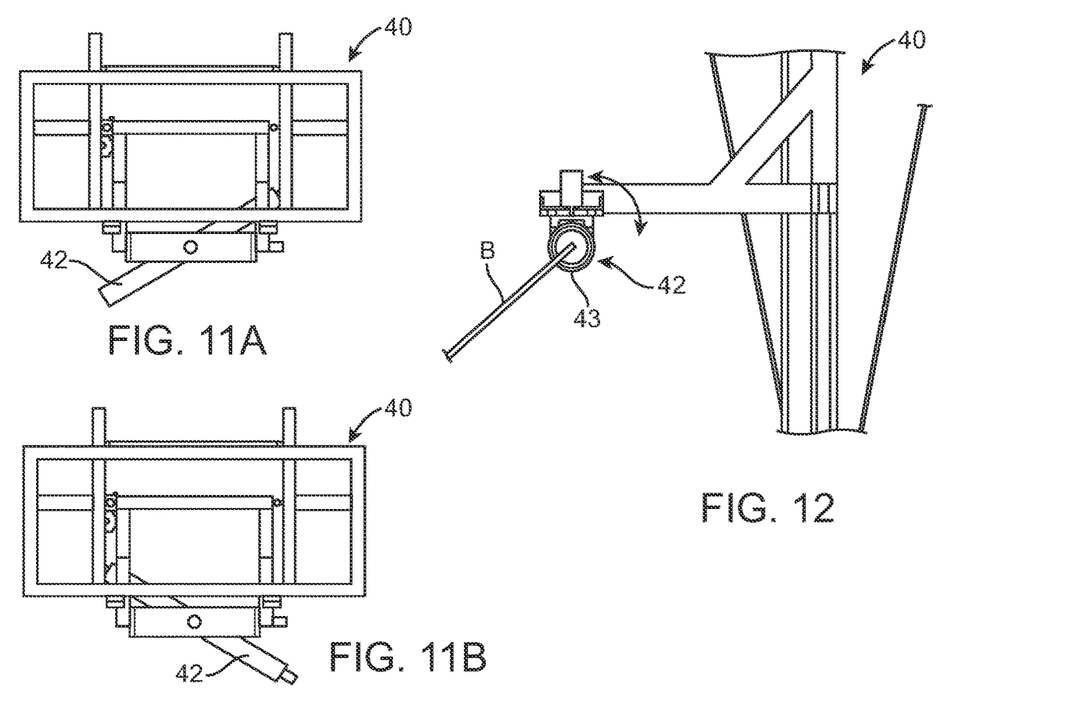
FIG. 11A is a top plan view of the detector arm showing the X-ray detector rotated about a vertical "yaw-axis" to point in a first direction.
FIG. 11B is a top plan view of the detector arm showing the X-ray detector rotated about a vertical "yaw-axis" to point in a second direction.
FIG. 12 is a side elevation view of the detector arm, showing the X-ray detector rotated about a "roll-axis" to align with an X-ray beam.

Next, FIGS. 11A and 11B are top plan views of detector arm 40 showing the X-ray detector 42 rotated about a vertical "yaw-axis" by positioning system 44 to point in a first direction (FIG. 11A) or a second direction (FIG. 11B).

FIG. 12 shows a side elevation view of detector arm 40, showing the X-ray detector 42 rotated about its "roll-axis" by positioning system 43.

Figure 13A:
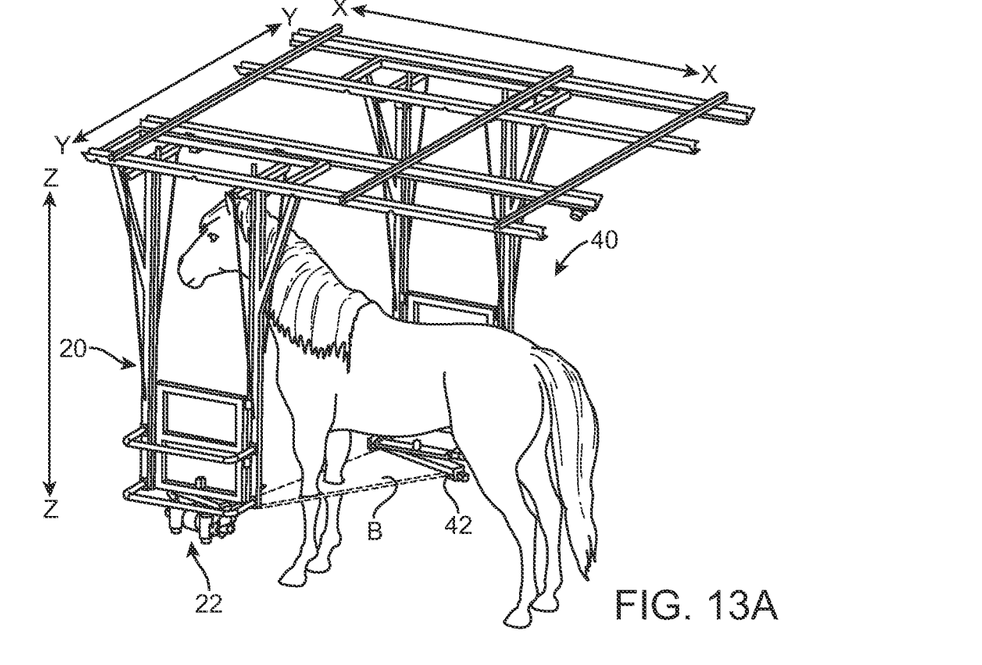
FIG. 13A is a rear top perspective view of an exemplary image being taken through a pair of horse's legs.
Figure 13B:
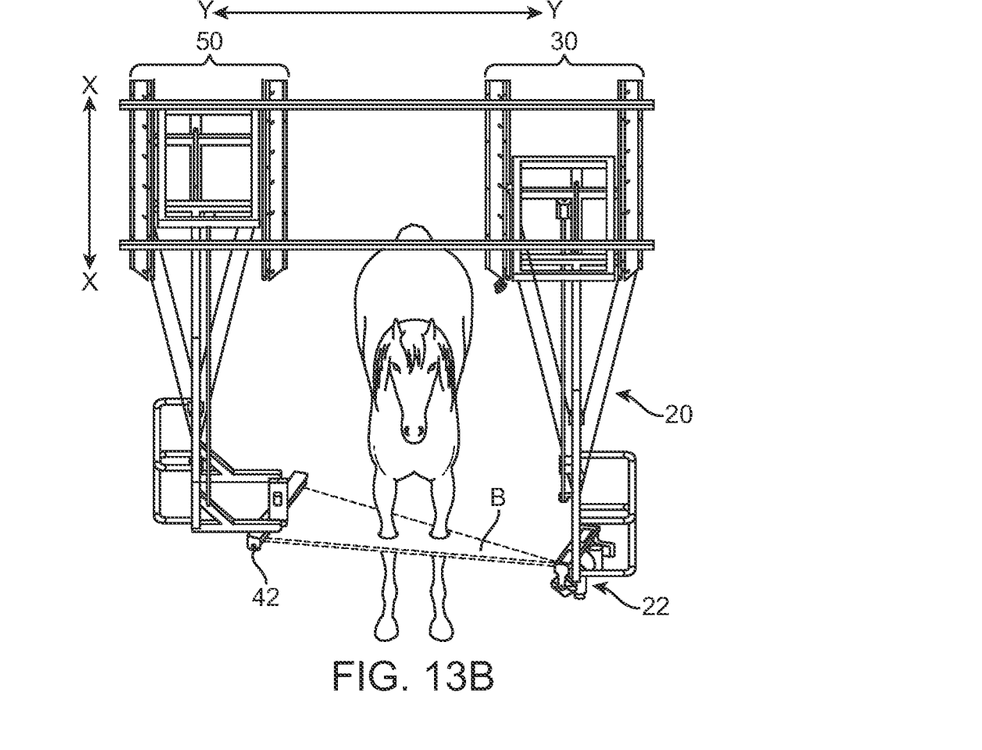
FIG. 13B is a front top perspective corresponding to FIG. 13A, showing the imaging system and horse in the same position, but viewed from a different angle.

FIGS. 13A and 13B is showing the imaging system 10 and horse in one position. The present system is ideally suited to acquire radiographic images of a sedated, standing horse and other large animals. The operator positions X-ray emitter 22 and X-ray detector 42 so that transmission x-ray images can be acquired of various anatomical views and features of the standing horse. Specifically, X-ray emitter 22 and X-ray detector 42 can be positioned such that the plane of the fan-shaped planar X-ray beam B is incident along the length of X-ray detector 42. Optionally, X-ray detector 42 is an elongated linear photodiode array covered by scintillating material. As also seen, X-ray detector 42 is preferably rotated so that the entire length of its array is aligned with the plane of fan-shaped beam B.

In optional embodiments, the separation distance between the two X-Z planes can be provided when one or both of arms 20 and 40 with a Y-axis assembly for increasing or decreasing the Y-axis separation distance between the assembly arms.

In preferred embodiments, a collimator 25 (FIG. 6) can be provided for producing a fan-shaped planar X-ray beam B. Collimator 25 prevents off-axis beam scattering. Advantageously, the use of a fan-shaped beam B can dramatically improve image quality, as compared to cone beam CT systems. As can be seen, the plane of fan-shaped planar X-ray beam B is moveable in yaw, pitch and roll directions. Collimator 25 may comprise a disk made of lead, tungsten or another high-z element or alloy, with the disk having a slot machined into it that can be rotated by roll-axis of motion positioning system 23 to rotate the orientation of the fan-shaped beam about an axis perpendicular to the roll-axis of X-ray emitter 22.

FIG. 14 is a schematic of an optional Modulated Amplitude Gain Intensity Control system 80 for use with the present system, as follows. Modulated Amplitude Gain Intensity Control System 80 includes an optional automatic exposure controller 82 that can adjust the x-ray exposure parameters during a scan to change the x-ray exposure parameters during the scan to compensate for changes in anatomic content during the scan. This feedback mechanism can be similar to existing automatic brightness control (ABS) features of fluoroscopic and serial radiographic imaging systems used in medical applications. To implement this function, a high performance embedded control PC can be used to synchronize and vary the image acquisition parameters of the x-ray camera, the x-ray flux (mA, kVp) of the generator and other beam filtering and conditioning media, selectable between lines during a scan. This process modulates the amplitude, gain and intensity of the acquired image as the anatomic thickness and density changes during each line of scan. The automatic exposure controller 82 communicates with the motion control computer 84 (to ascertain position and scan speed), the X-ray detector to receive image data and control the imaging parameters and master line clock, and a selectable attenuator/filter assembly.

The density of areas of anatomy to be acquired by the system may exceed the dynamic range of the x-ray camera. To be able to extend this dynamic range several techniques can be implemented to allow selection of best method during the scan. Preferably, there is a 2:1 gain control built into the camera electronics, the x-ray generator itself can be remotely programmable in both mAs and KVp. To allow for very rapid changes between lines, a small linear actuator (voice coil motor) and a filter stack (from 1 to several various filters or attenuator media are possible) can be attached in front of the rotating slit collimator 25 on the X-ray emitter head 22.

There are also areas of the anatomy that can be better visualized with a "hardened" beam, and the present system allows various x-ray profile altering materials to be introduced. A processor (not shown) of the system 80 preferably has the ability to read an entire line of image data, estimate anatomic trends and apply neighborhood estimation to set a combination of generator, filter, master camera line clock and scan speed adjustments.

The processor of the system 80 will preferably pass a set of metadata along with each line of data to a downstream image post-processor. The first stage of the post-processor will take this metadata and apply it to the last line acquired. In this way a single wide-dynamic-range image can be constructed. Once this composite image is created, and based on anatomical content and pre-selected presentation parameters, a final post-processed image can be prepared and presented to the operators display console. Here minor adjustments may be made, and the image or images sent to an external PACS (picture archiving and communications system) for long term storage and sharing.

During line scanning, the output of the x-ray tube is collimated down to a thin fan beam essentially blocking over 90% of the tube output. The present system is capable of acquiring images that are 2.5 meters long and 2 meters high, an area of 5 square meters. This is significantly larger than the largest area a projection radiography detector can do (17"×17" or <0.2 sq meters). Scan times using conventional medical radiography equipment can require up to 10 second exposures. Scanning speeds of the system can vary from <1 inch/second up to 10 inches/second.

Some views like the head-neck-thoracic spine (C1-T3) span an area of the horse where the density and thickness of the anatomy changes significantly. In order to acquire all of these anatomical features in a single exposure, the x-ray exposure parameters can change during the scan to optimize image quality for all components of the anatomy along the scan. This can be accomplished by using dynamic exposure control such as Fluoroscopy and Serial Radiographic imaging modes. A preferred embodiment of the X-ray emitter 22 tube is a Varex G-192 insert and a B-130H housing. The housing can optionally use an external cooling system such as the Varex HE-320 heat exchanger. A preferred embodiment of the x-ray generator is the CPI Indigo IQ (80 or 100 kW).

The preferred embodiment of the X-ray detector 42 can be a time-delayed-integration (TDI) version such as the model XTI90808 manufactured by X-Scan Corporation. This model has 8 rows of detectors that are 0.8 mm×0.8 mm. A scintillating material is applied to the surface of the detectors made of Cesium Iodide (CsI) or Cadmium Tungstate (CdWO$_4$). The scintillator material is 1.5 to 3 mm thick and made of individual crystals of pieces that are 0.75 mm square. A coating of epoxy doped with Titanium Oxide is applied to each piece of scintillator arranged in a block of pixelated scintillators (one for each detector on the LDA). This is done to prevent light generated in the scintillator from x-ray absorption from illuminating adjacent pixels. At the x-ray energies used with the LS-1 (<150 kVp) the scintillator can absorb over 95% of the incident x-rays.

A master motion controller can optionally consist of an embedded control program that can communication with all motor controllers to establish home positions, program multiple concurrent motion profiles and provide feedback based on derived resulting geometry to align and track X-ray emitter 22 source X-ray detector 42 before and during a scan using derived alignment points and a 3D position calculation algorithms to produce smooth trajectories for the x-ray source and LDA during a scan. Suitable tracking algorithms with active filters will attenuate the effects of vibration and other motion-induced tracking errors. Alternatively, or in conjunction, an active or dynamic control strategy could be employed where the motion-correction is achieved using a feedback control loop using output from a detector or X-ray detector 42 that samples the beam along its length during each scan.

An optional machine-vision sub-system can be incorporated into the motion controller to provide spatial information about the animal or object being scanned. This subsystem can include visible-light cameras and laser-based grid projectors. Accordingly, a series of fixed color cameras and simple lenses can be arranged to visualize the size (height, width, and length), real time position of the horse, and, potentially the position of the technical staff close to the mechanism and/or patient. Ascertaining the position of the horse, and knowing breed and demographics from the incoming patient exam order, the present system can take the requested (set of) view(s) and under computer control automatically calculate the spatial location of the patient's anatomy and derive the resulting scan path(s). This relieves the operator from having to enter reference points, etc.

A plurality of laser-based grid projectors, positioned to illuminate an anatomical area of interest can use the machine vision system detailed above, and the system can be enabled to image the resulting spatially-distorted grid pattern and, using a geometric deconvolution processor, calculate the physical surface dimensions of the patient. These measurements can be used for tracking variations in posture, changes in body size over time, anatomical changes that can be traced to normal or traumatic circumstances, or as a reference plane for creating a custom-fitted saddle, for example.

A system console can also be used required to provide a user interface where patient demographics can be entered prior to an exam, exam protocols can be chosen (for various anatomic views desired) and acquired images can be processed, displayed and archived. A commercial PC with an Intel i7 processor, a Graphics Processing Unit (GPU), 16 GBytes of RAM and a hard drive with 1 TByte of storage is adequate for the purposes of controlling the system as described with suitable custom software programs and applications. The output of the system console will be a newly defined LX DICOM object.

FIG. 15 illustrates a second embodiment of the present system, being an imaging system 100 comprising: a pair of multi-axis-of-motion X-ray emitter and detector arm assemblies 101, including: an X-ray emitter 108, an X-ray detector 104, and a positioning system 103 for: pointing X-ray emitter 108 and X-ray detector 104 up and down at different angles to a horizontal plane, and also moving X-ray emitter 108 and X-ray detector 104 up and down in a vertical direction. In the illustrated embodiment, X-ray detector 104 is curved. It is to be understood that X-ray detector 104 may also be flat, all keeping within the scope of the present invention. The pair of multi-axis-of-motion X-ray emitter and detector arm assemblies 101 are positioned facing one another (as shown) on either side of an object 102 such that: the X-ray emitter 108 on the positioning system 103 of the first multi-axis-of-motion X-ray emitter and detector arm assembly 101 projects an X-ray beam 106 on to the curved X-ray detector 104 on the positioning system 103 of the second multi-axis-of-motion X-ray emitter and detector arm assembly 101, and the X-ray emitter 108 on the positioning system 103 of the second multi-axis-of-motion X-ray emitter and detector arm assembly 101 projects an X-ray beam 106 back onto curved X-ray detector 104 on the positioning system 103 of the first multi-axis-of-motion X-ray emitter and detector arm assembly 101. As can be seen, X-ray emitter 108 is preferably positioned at a central location on the curved X-ray detector 104.

In many respects, the embodiment of the invention illustrated in FIG. 15 is equivalent to a floor mounted version of the ceiling mounted embodiment of the invention shown in FIGS. 1 to 14. As such, it is more compact and can be taken to various locations in the field (such as horse races or auctions).

The robotic arms that comprise positioning system 103 are similar to the positioning systems shown in FIGS. 1 to 14 in that the positioning system 103 are also preferably each individually adapted to rotate in roll, pitch and yaw directions, as well as being raised and lowered in the Z-direction. In addition, the positioning system 103 are also preferably configured to move together/apart in the Y-direction. Movement in the Y-direction (i.e.: into and out of the page) is also possible.

Preferably, positioning system 103 are mounted onto robotic bases. When under computer control, the positioning system 103 are optionally configured for rotating the X-ray emitter 108 and the curved X-ray detector 104 around a horizontal axis for pointing the X-ray emitter and the curved X-ray detector in different directions in a vertical plane. Preferably, each moveable robotic base is either positionable on wheels, or positionable on a pair of rails. In preferred embodiments, the positioning system 103 for each of the pair of multi-axis-of-motion X-ray emitter and detector arm assemblies 101 are configured for moving the X-ray emitter 108 and the curved X-ray detector 104 back and forth in a horizontal X-direction (i.e.: in and out of the page as illustrated). This permits the operator to take successive image slices through the horse to produce volumetric images. Optionally, the rails could have encoders to track the location of robotic bases, or machine vision systems 107 can be used to determine locations.

It is to be understood that the system illustrated in FIG. 15 can be used to perform both regular 2D "static" or "plain film" radiography, as well as to provide a system for providing 3D radiographic imaging.

The curved detector arrays 104 are preferably positioned a distance apart such that an arc with a radius of curvature equal to the diameter of a circle passing through the detector arrays 104. (Typically, this distance will be between 4 and 6 feet; i.e.: large enough to accommodate the width of a horse standing therebetween). Most preferably, the length of each curved detector 104 is ¼ of the circle of rotation of a C-arm. It is to be understood, however, that the present system is not limited to this geometry.

Optionally, the positioning system 103 for each of the pair of multi-axis-of-motion X-ray emitter and detector arm assemblies 101 are also configured for rotating the X-ray emitter 108 and the curved X-ray detector 104 around a vertical axis for pointing the X-ray emitter 108 and the curved X-ray detector 104 in different directions in a horizontal plane. This is useful when the positioning system 103 or robotic bases are positioned at different.

In this second embodiment, electronics are also provided to control the diode array, perform calibration functions and export an image to a system controller for post processing, archiving and display.

What is claimed is:

1. An X-ray imaging system, comprising:
   (a) a multi-axis of motion X-ray emitter arm assembly, including:
      (i) an X-ray emitter,
      (ii) a yaw-axis of motion positioning system for pointing the X-ray emitter in different directions in a horizontal plane,
      (iii) a pitch-axis of motion positioning system for pointing the X-ray emitter up and down at different angles to a horizontal plane,
      (iv) a Z-axis assembly for moving the X-ray emitter up and down in a vertical direction;
      (v) an X-axis assembly for moving the X-ray emitter back and forth in a horizontal direction; and
      (vi) a roll-axis of motion positioning system for rotating the X-ray emitter; and
   (b) a multi-axis of motion X-ray detector arm assembly, including:
      (i) an X-ray detector,
      (ii) a yaw-axis of motion positioning system for pointing the X-ray detector in different directions in a horizontal plane,
      (iii) a pitch-axis of motion positioning system for pointing the X-ray detector up and down at different angles to a horizontal plane,
      (iv) a Z-axis assembly for moving the X-ray detector up and down in a vertical direction; and
      (v) an X-axis assembly for moving the X-ray detector back and forth in a horizontal direction; and
      (vi) a roll-axis of motion positioning system for rotating the X-ray detector.

2. The X-ray imaging system of claim 1, wherein the X-ray emitter is mounted onto the pitch-axis of motion positioning system of the multi-axis of motion X-ray emitter arm assembly, and the pitch-axis of motion positioning system of the multi-axis of motion X-ray emitter arm assembly is mounted onto the yaw-axis of motion positioning system of the multi-axis of motion X-ray emitter arm assembly, and wherein the yaw-axis of motion positioning system of the multi-axis of motion X-ray emitter arm assembly is mounted onto the Z-axis assembly of the multi-axis of motion X-ray emitter arm assembly, and the Z-axis assembly of the multi-axis of motion X-ray emitter arm assembly is mounted onto the X-axis assembly of the multi-axis of motion X-ray emitter arm assembly.

3. The X-ray imaging system of claim 1, wherein the X-ray detector is mounted onto the pitch-axis of motion positioning system of the multi-axis of motion X-ray detector arm assembly, and the pitch-axis of motion positioning system of the multi-axis of motion X-ray detector arm assembly is mounted onto the yaw-axis of motion positioning system of the multi-axis of motion X-ray detector arm assembly, and wherein the yaw-axis of motion positioning system of the multi-axis of motion X-ray detector arm assembly is mounted onto the Z-axis assembly of the multi-axis of motion X-ray detector arm assembly, and the Z-axis assembly is mounted onto the X-axis assembly of the multi-axis of motion X-ray detector arm assembly.

4. The X-ray imaging system of claim 1, wherein the X-ray emitter and the X-ray detector can each be moved to different positions in opposing vertical planes.

5. The X-ray imaging system of claim 4, wherein the X-ray emitter and the X-ray detector can each be tilted to directly face one another.

6. The X-ray imaging system of claim 1, wherein the multi-axis of motion X-ray emitter arm assembly further comprises: (vii) a collimator for producing a fan-shaped planar X-ray beam.

7. The X-ray imaging system of claim 6, wherein a plane of the fan-shaped planar X-ray beam is moveable in yaw, pitch, and roll directions.

8. The X-ray imaging system of claim 7, wherein the X-ray emitter and X-ray detector can be positioned such that the plane of the fan-shaped planar X-ray beam is incident along a length of the X-ray detector.

9. The X-ray imaging system of claim 1, wherein the X-ray detector comprises a scintillator material and an elongated linear photodiode array covered by the scintillating material.

10. The X-ray imaging system of claim 1, wherein the X-axis assembly of the multi-axis of motion X-ray emitter arm assembly and the X-axis assembly of the multi-axis of motion X-ray detector arm assembly for moving the X-ray emitter and the X-ray detector are mounted onto a ceiling of a room.

11. An X-ray imaging system, comprising:
   (a) a first multi-axis of motion X-ray emitter and detector arm assembly, including:
      (i) an X-ray emitter,
      (ii) an X-ray detector, and
      (iii) a positioning system for:
         (A) pointing the X-ray emitter and the X-ray detector up and down at different angles to a horizontal plane, and
         (B) moving the X-ray emitter and the X-ray detector up and down in a vertical direction; and
   (b) a second multi-axis of motion X-ray emitter and detector arm assembly, including:
      (i) an X-ray emitter,
      (ii) an X-ray detector, and
      (iii) a positioning system for:
         (A) pointing the X-ray emitter and the X-ray detector up and down at different angles to a horizontal plane, and
         (B) moving the X-ray emitter and the X-ray detector up and down in a vertical direction;
   wherein the first multi-axis of motion X-ray emitter and detector arm assembly and the second multi-axis of motion X-ray emitter and detector arm assembly are positioned facing one another such that:
the X-ray emitter on the first multi-axis of motion X-ray emitter and detector arm assembly projects an X-ray beam on to the X-ray detector on the second multi-axis of motion X-ray emitter and detector arm assembly, and
the X-ray emitter on the second multi-axis of motion X-ray emitter and detector arm assembly projects an X-ray beam on to the X-ray detector on the first multi-axis of motion X-ray emitter and detector arm assembly.

12. The X-ray imaging system of claim 11, wherein each of the positioning system of the first multi-axis of motion X-ray emitter and detector arm assembly and the positioning system of the second multi-axis of motion X-ray emitter and detector arm assembly comprise a robotic arm.

13. The X-ray imaging system of claim 11, wherein each of the positioning system of the first multi-axis of motion X-ray emitter and detector arm assembly and the positioning system of the second multi-axis of motion X-ray emitter and detector arm assembly is configured for: (C) rotating the X-ray emitter and the X-ray detector around a vertical axis for pointing the X-ray emitter and the X-ray detector in different directions in a horizontal plane.

14. The X-ray imaging system of claim 11, wherein each of the positioning system of the first multi-axis of motion X-ray emitter and detector arm assembly and the positioning system of the second multi-axis of motion X-ray emitter and detector arm assembly is configured for: (D) moving the X-ray emitter and the X-ray detector back and forth in a horizontal direction.

15. The X-ray imaging system of claim 14, wherein each of the positioning system of the first multi-axis of motion X-ray emitter and detector arm assembly and the positioning system of the second multi-axis of motion X-ray emitter and detector arm assembly configured for moving the X-ray emitter and the X-ray detector back and forth in a horizontal direction comprises wheels on a robotic base or rails on the ground.

16. The X-ray imaging system of claim 11, farther comprising a first moveable robotic base and a second moveable robotic base, wherein the first multi-axis of motion X-ray emitter and detector arm assembly is mounted on the first moveable robotic base and the second multi-axis of motion X-ray emitter and detector arm assembly is mounted on the second moveable robotic base.

17. The X-ray imaging system of claim 11, wherein each of the X-ray detector of the first multi-axis of motion X-ray emitter and detector arm assembly and the X-ray detector of the second multi-axis of motion X-ray emitter and detector arm assembly is curved and are positioned a distance apart such that an arc with a radius of curvature equal to a diameter of a circle passes through the X-ray detector of the first multi-axis of motion X-ray emitter and detector arm assembly and the X-ray detector of the second multi-axis of motion X-ray emitter and detector arm assembly.

18. The X-ray imaging system of claim 17, wherein each curved X-ray detector comprises a C-arm, wherein a length of each curved X-ray detector is ¼ of a circle of rotation of the C-arm.

19. An X-ray imaging system, comprising:
(a) a first arm assembly, including:
    (i) a pitch-axis-of-motion positioning system,
    (ii) a Z-axis-old-motion positioning system,
    (iii) an X-axis of motion positioning system,
    (iv) a yaw-axis-of-motion positioning system, and
    (v) a roll-axis-of-motion positioning system; and
(b) a second arm assembly, including:
    (i) a pitch-axis-of-motion positioning system,
    (ii) a Z-axis-of-motion positioning system,
    (iii) ail X-axis of motion positioning system,
    (iv) a yaw-axis-of-motion positioning system, and
    (v) a roll-axis-of-motion positioning system; and
wherein each of the first arm assembly and second arm assembly is independently positionable.

20. The X-ray imaging system of claim 19, wherein the first arm assembly further comprises an X-ray emitter thereon and the second arm assembly further comprises an X-ray detector thereon.

21. The X-ray imaging system of claim 19, wherein each of the first arm assembly and the second arm assembly comprises both an X-ray emitter and an X-ray detector thereon.

* * * * *